(12) United States Patent
Rahdert et al.

(10) Patent No.: US 8,142,494 B2
(45) Date of Patent: Mar. 27, 2012

(54) DEVICES, SYSTEMS, AND METHODS FOR RETAINING A NATIVE HEART VALVE LEAFLET

(75) Inventors: David A. Rahdert, San Francisco, CA (US); John A. Macoviak, La Jolla, CA (US); Timothy R. Machold, Moss Beach, CA (US); Robert T. Chang, Belmont, CA (US); Rick A. Soss, Burlingame, CA (US)

(73) Assignee: MVRx, Inc., Moss Beach, CA (US)

( * ) Notice: Subject to any disclaimer, the term of this patent is extended or adjusted under 35 U.S.C. 154(b) by 0 days.

(21) Appl. No.: 12/386,821

(22) Filed: Apr. 23, 2009

(65) Prior Publication Data
US 2009/0228099 A1  Sep. 10, 2009

Related U.S. Application Data

(60) Division of application No. 10/676,729, filed on Oct. 1, 2003, now Pat. No. 7,527,646, and a continuation-in-part of application No. 09/666,617, filed on Sep. 20, 2000, now Pat. No. 6,893,459, and a continuation-in-part of application No. PCT/US02/31376, filed on Oct. 1, 2002.

(60) Provisional application No. 60/326,590, filed on Oct. 1, 2001, provisional application No. 60/429,444, filed on Nov. 26, 2002, provisional application No. 60/429,709, filed on Nov. 26, 2002, provisional application No. 60/429,462, filed on Nov. 26, 2002.

(51) Int. Cl.
*A61F 2/24* (2006.01)

(52) U.S. Cl. ...................................... 623/2.36

(58) Field of Classification Search ........ 623/2.36–2.38, 623/1.26, 1.34, 1.36, 2.14, 2.18; 606/151, 606/14, 41, 52, 76
See application file for complete search history.

(56) References Cited

U.S. PATENT DOCUMENTS

| 4,056,854 A | 11/1977 | Boretos et al. |
| 4,275,469 A | 6/1981 | Gabbay |
| 4,994,069 A | 2/1991 | Ritchart et al. |
| 5,360,444 A | 11/1994 | Kusuhara |
| 5,370,685 A | 12/1994 | Stevens |
| 5,545,241 A | 8/1996 | Vanderauwera et al. |
| 5,716,397 A | 2/1998 | Myers |
| 5,776,189 A | 7/1998 | Khalid |
| 5,792,155 A | 8/1998 | Van Cleef |
| 5,830,224 A | 11/1998 | Cohn et al. |

(Continued)

OTHER PUBLICATIONS

Templeton III, et al. "Experimental Reconstruction of Cardiac Valves by Venous and Pericardial Grafts." Annals of Surgery vol. 129, No. 2, Feb. 1949, 161-176.

(Continued)

*Primary Examiner* — Alvin J Stewart
(74) *Attorney, Agent, or Firm* — Ryan Kromholz & Manion, S.C.

(57) ABSTRACT

Devices, systems and methods retain a native heart valve leaflet to prevent retrograde flow. The devices, systems, and methods employ an implant that, in use, rests adjacent a valve annulus and includes a retaining structure that is sized and shaped to overlay at least a portion of one or more native valve leaflets. The retaining structure retains the leaflet or leaflets it overlays, to resist leaflet eversion and/or prolapse. In this way, the implant prevents or reduces regurgitation. The implant does not interfere significantly with the opening of and blood flow through the leaflets during periods of antegrade flow.

13 Claims, 13 Drawing Sheets

U.S. PATENT DOCUMENTS

| Patent | Date | Inventor | Ref |
|---|---|---|---|
| 5,855,601 A | 1/1999 | Bessler et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,260,552 B1 | 7/2001 | Mortier et al. | |
| 6,261,222 B1 | 7/2001 | Schweich, Jr. et al. | |
| 6,299,637 B1 | 10/2001 | Shaolian et al. | 623/1.24 |
| 6,312,464 B1 | 11/2001 | Navia | |
| 6,332,864 B1 | 12/2001 | Schweich, Jr. et al. | |
| 6,332,893 B1 | 12/2001 | Mortier et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | 623/1.24 |
| 6,503,272 B2 | 1/2003 | Duerig et al. | 623/1.24 |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 | 10/2003 | St. Goar et al. | |
| 6,656,221 B2 | 12/2003 | Taylor et al. | |
| 6,669,709 B1 | 12/2003 | Cohn et al. | |
| 6,676,699 B2 | 1/2004 | Shiu | 623/1.24 |
| 6,676,702 B2* | 1/2004 | Mathis | 623/2.36 |
| 6,685,739 B2 | 2/2004 | DiMatteo et al. | 623/1.24 |
| 6,702,826 B2 | 3/2004 | Liddicoat et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,824,562 B2* | 11/2004 | Mathis et al. | 623/2.36 |
| 6,913,608 B2 | 7/2005 | Liddicoat et al. | |
| 6,945,978 B1 | 9/2005 | Hyde | |
| 7,004,176 B2 | 2/2006 | Lau | |
| 7,070,618 B2* | 7/2006 | Streeter | 623/2.36 |
| 7,166,127 B2* | 1/2007 | Spence et al. | 623/2.37 |
| 7,291,168 B2* | 11/2007 | Macoviak et al. | 623/2.36 |
| 7,527,646 B2* | 5/2009 | Rahdert et al. | 623/2.36 |
| 2001/0010017 A1 | 7/2001 | Letac et al. | |
| 2001/0021872 A1* | 9/2001 | Bailey et al. | 623/1.24 |
| 2001/0051824 A1 | 12/2001 | Hopkins et al. | |
| 2002/0032481 A1 | 3/2002 | Gabbay | |
| 2002/0065554 A1* | 5/2002 | Streeter | 623/2.36 |
| 2002/0087169 A1* | 7/2002 | Brock et al. | 606/139 |
| 2002/0094573 A1 | 7/2002 | Bell | |
| 2002/0123802 A1 | 9/2002 | Snyders | |
| 2002/0129820 A1* | 9/2002 | Ryan et al. | 128/858 |
| 2002/0138138 A1 | 9/2002 | Yang | |
| 2003/0014104 A1* | 1/2003 | Cribier | 623/2.11 |
| 2003/0040792 A1 | 2/2003 | Gabbay | |
| 2003/0069636 A1* | 4/2003 | Solem et al. | 623/2.37 |
| 2003/0078654 A1* | 4/2003 | Taylor et al. | 623/2.36 |
| 2003/0120340 A1 | 6/2003 | Liska et al. | |
| 2003/0212453 A1* | 11/2003 | Mathis et al. | 623/2.11 |
| 2003/0233022 A1 | 12/2003 | Vidlund et al. | |
| 2004/0049211 A1* | 3/2004 | Tremulis et al. | 606/153 |
| 2004/0127982 A1* | 7/2004 | Machold et al. | 623/2.36 |
| 2004/0148019 A1 | 7/2004 | Vidlund et al. | |
| 2004/0243230 A1* | 12/2004 | Navia et al. | 623/2.36 |
| 2004/0260393 A1* | 12/2004 | Rahdert et al. | 623/2.36 |
| 2005/0004668 A1* | 1/2005 | Aklog et al. | 623/2.36 |
| 2005/0010287 A1* | 1/2005 | Macoviak et al. | 623/2.36 |
| 2005/0038508 A1* | 2/2005 | Gabbay | 623/2.36 |
| 2005/0055089 A1* | 3/2005 | Macoviak et al. | 623/2.37 |
| 2005/0107810 A1* | 5/2005 | Morales et al. | 606/143 |
| 2006/0241745 A1 | 10/2006 | Solem | |

OTHER PUBLICATIONS

Moore et al. "Unsuitability of Transventricular Autogenous Slings for Diminishing Valirular Insufficiency." Surgery, vol. 33, No. 2, Feb. 1953, 173-182.

Murray et al. "Reconstruction of the Valves of the Heart." The Canadian Medical Association Journal, vol. 38, No. 4, Apr. 1938, 317-319.

Bolling et al. "Early Outcome of Mitral Valve Reconstruction in Patients With End-Stage Cardiomyopathy." J Thorac Cardiovasc Surg 1995; 109:676-683.

Kameda et al. "Annuloplasty for Severe Mitral Regurgitation Due to Dilated Cardiomyopathy." Ann Thorac Surg 1996; 61:1829-1832.

Bolling et al. "Intermediate-Term Outcome of Mitral Reconstruction in Cardiomyopathy." Journal of Thoracic Cardiovascular Surgery, vol. 115, No. 2, Feb. 1998, 381-388.

Harlan et al. Manual of Cardiac Surgery, vol. 2, 1981 Figs. 16.3-16.4.

Edmunds, Jr. et al. "Septal Defect." Atlas of Cardiothoracic Surgery 1990.

Koniaris, MD et al. "Dynamic Retention: A Technique for Closure of the Complex Abdomen in Critically Ill Patients." Archives of Surgery, vol. 136, No. 12, Dec. 2001, 1359-1362.

Fucci et al. "Improved Results With Mitral Valve Repair Using New Surgical Techniques." European Journal of Cardio-Thoracic Surgery, vol. 9, 1995, 621-626.

Davila et al. "Circumferential Suture of the Mitral Ring: A Method for the Surgical Correction of Mitral Insufficiency." Journal of Thoracic Surgery Nov. 1955; 30(5): 531-60.

Harken et al. "The Surgical Correction of Mitral Insufficiency" Journal of Thoracic Surgery. Dec. 1954; 28(6):604-24.

Kuykendall et al. "Surgical Correction of Chronic Mitral Insufficiency in Dogs." Surgery. Oct. 1958; 44(4):718-25.

Harken et al. "The Surgical Correction of Mitral Insufficiency." Surgical Forum 4:4-7 1953.

Davila et al. "A Method for the Surgical Correction of Mitral Insufficiency." Surgery, Gynecology and Obstetrics Apr. 1954; 98(4):407-12.

Davila et al. "The Clinical and Physiologic Criteria for Surgical Correction of Mitral Insufficiency." Journal of Thoracic Surgery Feb. 1958; 35(2):206-31.

Glover et al. "The Treatment of Mitral Insufficiency by the Purse-String Technique." Journal of Thoracic Surgery Jan. 1957; 33(1): 75-101.

Rankin et al. "A Clinical Comparison of Mitral Valve Repair Versus Valve Replacement in Ischemic Mitral Regurgitation." J Thorac Cardiovasc Surg. Feb. 1988; 95(2):165-77.

Barnard et al. "A Surgical Approach to Mitral Insufficiency." Br J Surg. May 1961; 48:655-62.

McKenzie et al. "Current Concepts in Surgical Correction of Acquired Mitral Insufficiency."Circulation. Oct. 1963; 28:603-16.

Saab et al. "Left Ventricular Aneurysm: A New Surgical Approach." Thorac Cardiovasc Surg. Feb. 1989; 37(1):11-9.

Cicek et al. "Left Ventricular Endoaneurysmorrhaphy: Effect on Left Ventricular Size, Shape and Function." Cardiology. Jul.-Aug. 1997; 88(4):340-5.

Liedtke et al. "Functional Reductions in Left Ventricular Volume." J Thorac Cardiovasc Surg. Feb. 1976; 71(2):195-206.

Sosa et al. "Recurrent Ventricular Tachycardia Associated With Postinfarction Aneurysm. Results of Left Ventricular Reconstruction." J Thorac Cardiovasc Surg. May 1992; 103(5); 855-60.

Cooley, "Repair of Postinfarction Ventricular Septal Defect." J Card Surg. Jul. 1994; 9(4):427-9.

Jatene, "Left Ventricular Aneurysmectomy. Resection or Reconstruction." J Thorqc Cardiovasc Surg 1985; 89:321-31.

de Silva et al. "Postinfarction Ventricular Septal Defect. An Efficacious Technique for Early Surgical Repair." J Throac Cardiovasc Surg. Jan. 1989; 97(1):86-9.

Tashiro et al. "Extended Endocardial Repair of Postinfarction Ventricular Septal Rupture: New Operative Technique-Modification of the Komeda-David Operation." J Card Surg. Mar. 1994; 9(2):97-102.

Daggett, "Surgical Technique for Early Repair of Posterior Ventricular Septal Rupture." J Thorac Cardiovasc Surg. Aug. 1982;84(2):306-12.

Daggett et al. "Surgery for Post-Myorcardial Infarct Ventricular Septal Defect." Ann Surg. Sep. 1977;186(3):260-71.

Dor, "Left Ventricular Aneurysms: the Endoventricular Circular Patch Plasty." Semin Thorac Cardiovasc Surg. Apr. 1997;9(2):123-30.

Antunes, "Submitral Left Ventricular Aneurysms. Correction by a New Transatrial Approach." J Thorac Cardiovasc Surg. Aug. 1987;94(2):241-5.

Alvarez et al. "Technical Improvements in the Repair of Acute Postinfarction Ventricular Septal Rupture." J Card Surg. Sep. 1992;7(3):198-202.

Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.

Skillington et al. "Surgical Treatment for Infarct-Related Ventricular Septal Defects. Improved Early Results Combined with Analysis of Late Functional Status." J thorac Cardiovasc Surg. May 1990;99(5):798-808.

Salati et al. "Severe Diastolic Dysfunction After Endoventriculoplasty." J Thorac Cardiovasc Surg. Apr. 1995;109(4):694-701.

Yacoub et al. "Anatomic Correction of the Syndrome of Prolapsing Right Coronary Aortic Cusp, Dilatation of the Sinus of Valsalva, and Ventricular Septal Defect." J thorac Cardiovasc Surg. Feb. 1997:113(7).743-60.

Bailey, et al. "Surgical Repair of Mitral Insufficiency." Diseases of the Chest, vol. XIX, No. 2, Feb. 1951, 125-137.

Henderson, et al., "The Surgical Treatment of Mitral Insufficiency." Experimental Use of Transplanted Pericardium in Dogs. Surgery 33(6):858-868; 1953.

Sakakibara, "A Surgical Approach to the Correction of Mitral Insufficiency."Annals of Surgery. vol. 142, No. 2, Aug. 1955, 196-203.

Harken et al. "The Surgical Correction of Mitral Insufficiency." The Journal of Thoracic Surgery. 28(6):604-627., 1954.

Bailey et al. "The Surgical Correction of Mitral Insufficiency by the Use of Pericardial Grafts." The Journal of Thoracic Surgery, vol. 28, No. 6, Dec. 1954, 551-603.

Kay et al. "Surgical Treatment of Mitral Insufficiency." Surgery. vol. 37, No. 5. May 1955, 697-706.

* cited by examiner

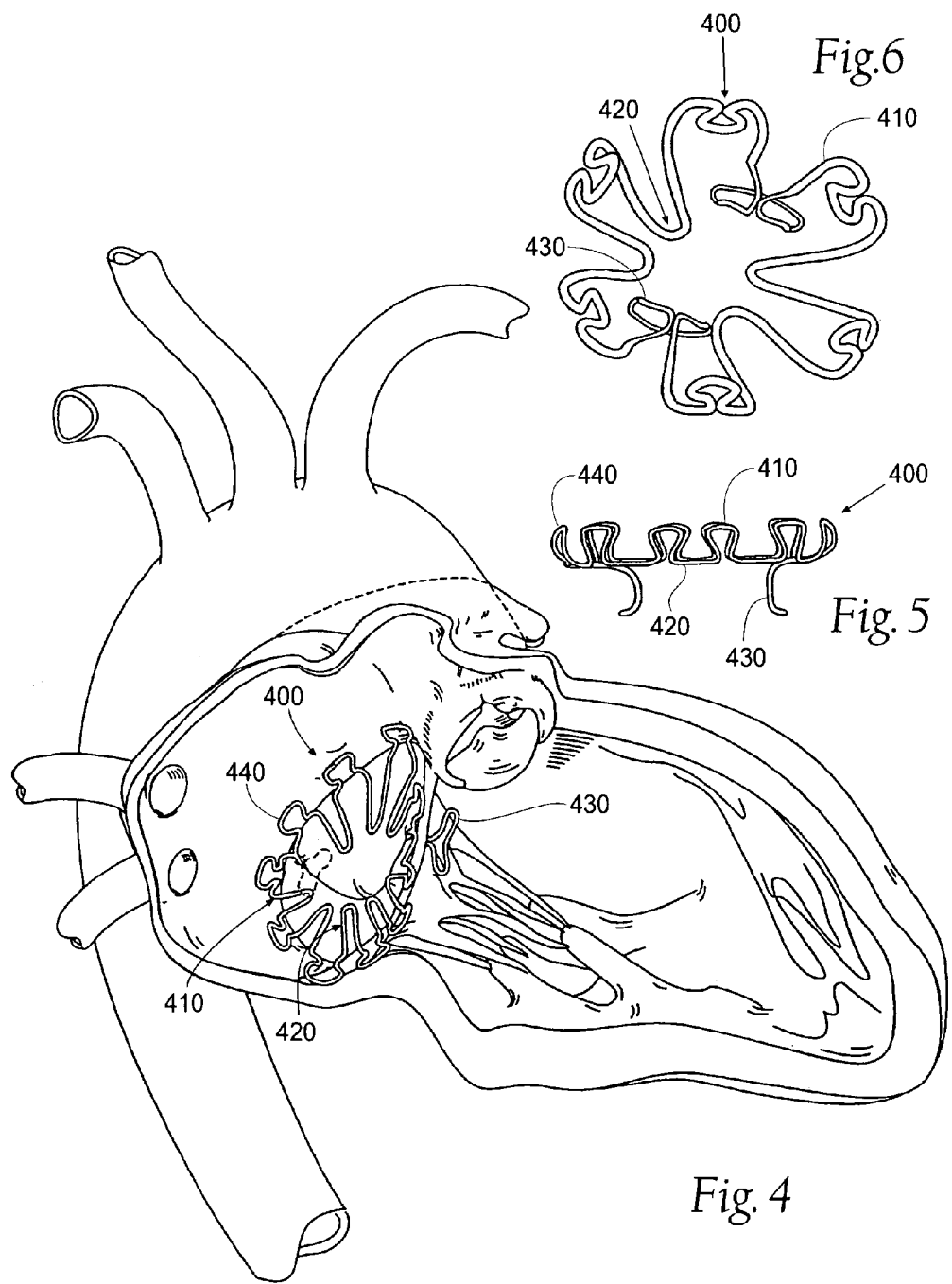

DEVICES, SYSTEMS, AND METHODS FOR RETAINING A NATIVE HEART VALVE LEAFLET

RELATED APPLICATIONS

This application is a divisional of U.S. patent application Ser. No. 10/676,729, filed Oct. 1, 2003 now U.S. Pat. No. 7,527,646, and entitled "Devices, Systems, and Methods for Retaining a Native Heart Valve Leaflet."

This application is also a continuation-in-part of U.S. patent application Ser. No. 09/666,617, filed Sep. 20, 2000, now U.S. Pat. No. 6,893,459 and dated May 17, 2005, and entitled "Heart Valve Annulus Device and Methods of Using Same."

This application is also a continuation-in-part of Patent Cooperation Treaty Application Serial No. PCT/US 02/31376, filed Oct. 1, 2002 and entitled "Systems and Devices for Heart Valve Treatments," which claimed the benefit of U.S. Provisional Patent Application Ser. No. 60/326, 590, filed Oct. 1, 2001.

This application also claims the benefit of U.S. Provisional Application Ser. No. 60/429,444, filed Nov. 26, 2002, and entitled "Heart Valve Remodeling Devices;" U.S. Provisional Patent Application Ser. No. 60/429,709, filed Nov. 26, 2002, and entitled "Neo-Leaflet Medical Devices;" and U.S. Provisional Patent Application Ser. No. 60/429,462, filed Nov. 26, 2002, and entitled "Heart Valve Leaflet Retaining Devices," all of the above which are each incorporated herein by reference.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1B) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 1B and 1C) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 1B), the aortic and pulmonary valves are closed to prevent back flow from the arteries into the ventricles. Shortly thereafter, the tricuspid and mitral valves open (as FIG. 1B shows), to allow flow from the atria into the corresponding ventricles. Shortly after ventricular systole (i.e., ventricular emptying) begins, the tricuspid and mitral valves close (see FIG. 1C)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

FIG. 1D shows a posterior oblique cutaway view of a healthy human heart 100. Two of the four heart chambers are shown, the left atrium 170, and the left ventricle 140 (not shown are the right atrium and right ventricle). The left atrium 170 fills with blood from the pulmonary veins. The blood then passes through the mitral valve (also known as the bicuspid valve, and more generally known as an atrioventricular valve) during ventricular diastole and into the left ventricle 140. During ventricular systole, the blood is then ejected out of the left ventricle 140 through the aortic valve 150 and into the aorta 160. At this time, the mitral valve should be shut so that blood is not regurgitated back into the left atrium.

The mitral valve consists of two leaflets, an anterior leaflet 110, and a posterior leaflet 115, attached to chordae tendineae 120 (or chords), which in turn are connected to papillary muscles 130 within the left atrium 140. Typically, the mitral valve has a D-shaped anterior leaflet 110 oriented toward the aortic valve, with a crescent shaped posterior leaflet 115. The leaflets intersect with the atrium 170 at the mitral annulus 190.

In a healthy heart, these muscles and their chords support the mitral and tricuspid valves, allowing the leaflets to resist the high pressure developed during contractions (pumping) of the left and right ventricles. In a healthy heart, the chords become taut, preventing the leaflets from being forced into the left or right atria and everted. Prolapse is a term used to describe the condition wherein the coaptation edges of each leaflet initially may coapt and close, but then the leaflets rise higher and the edges separate and the valve leaks. This is normally prevented by contraction of the papillary muscles and the normal length of the chords. Contraction of the papillary muscles is simultaneous with the contraction of the ventricle and serves to keep healthy valve leaflets tightly shut at peak contraction pressures exerted by the ventricle.

II. Characteristics and Causes of Mitral Valve Dysfunction

Valve malfunction can result from the chords becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

FIG. 2 shows a cutaway view of a human heart 200 with a prolapsed mitral valve. The prolapsed valve does not form a tight seal during ventricular systole, and thus allows blood to be regurgitated back into the left atrium during ventricular contraction. The anterior 220 and posterior 225 leaflets are shown rising higher than normal (i.e., prolapsing) into the left atrium. The arrows indicate the direction of regurgitant flow. Among other causes, regurgitation can result from redundant valve leaflet tissue or from stretched chords 210 that are too long to prevent the leaflets from being blown into the atrium. As a result, the leaflets do not form a tight seal, and blood is regurgitated into the atrium.

FIG. 3 shows a cutaway view of a human heart 300 with a flailing mitral valve 320. The flailing valve also does not form a tight seal during ventricular systole. Blood thus regurgitates back into the left atrium during ventricular contraction, as indicated by the arrows. Among other causes, regurgitation can also result from torn chords 310.

As a result of regurgitation, "extra" blood back flows into the left atrium. During subsequent ventricular diastole (when the heart relaxes), this "extra" blood returns to the left ventricle, creating a volume overload, i.e., too much blood in the left ventricle. During subsequent ventricular systole (when the heart contracts), there is more blood in the ventricle than expected. This means that: (1) the heart must pump harder to move the extra blood; (2) too little blood may move from the heart to the rest of the body; and (3) over time, the left ventricle may begin to stretch and enlarge to accommodate the larger volume of blood, and the left ventricle may become weaker.

Although mild cases of mitral valve regurgitation result in few problems, more severe and chronic cases eventually weaken the heart and can result in heart failure. Mitral valve regurgitation can be an acute or chronic condition. It is sometimes called mitral insufficiency.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

To date, invasive, open heart surgical approaches have been used to repair or replace the mitral valve with either a mechanical valve or biological tissue (bioprosthetic) taken from pigs, cows or horses.

The need remains for simple, cost-effective, and less invasive devices, systems, and methods for treating dysfunction of a heart valve, e.g., in the treatment of mitral valve regurgitation.

SUMMARY OF THE INVENTION

The invention provides devices, systems and methods that retain a native heart valve leaflet. The devices, systems, and methods include an implant that, in use, rests adjacent all or a portion of a valve annulus. The implant includes a retaining structure that is shaped to overlay at least a portion of one or more native valve leaflets. The implant further includes spaced-apart struts sized and configured to contact tissue near or within the heart valve annulus. The struts brace the retaining structure to resist leaflet eversion and/or prolapse. In this way, the implant prevents or reduces retrograde flow and regurgitation. The implant does not interfere with the opening of and blood flow through the leaflets during antegrade flow.

Other features and advantages of the invention shall be apparent based upon the accompanying description, drawings, and claims.

DESCRIPTION OF THE DRAWINGS

FIG. 4 is a perspective, anatomic view of a wire form implant that includes a retaining element to resist eversion and/or prolapse of a native valve leaflet, the implant being shown installed on a mitral valve annulus.

FIG. 5 is a side elevation view of the implant shown in FIG. 4, shown outside of the body.

FIG. 6 is a top view of the implant shown in FIG. 4, shown outside the body.

DETAILED DESCRIPTION

Figure 1A:
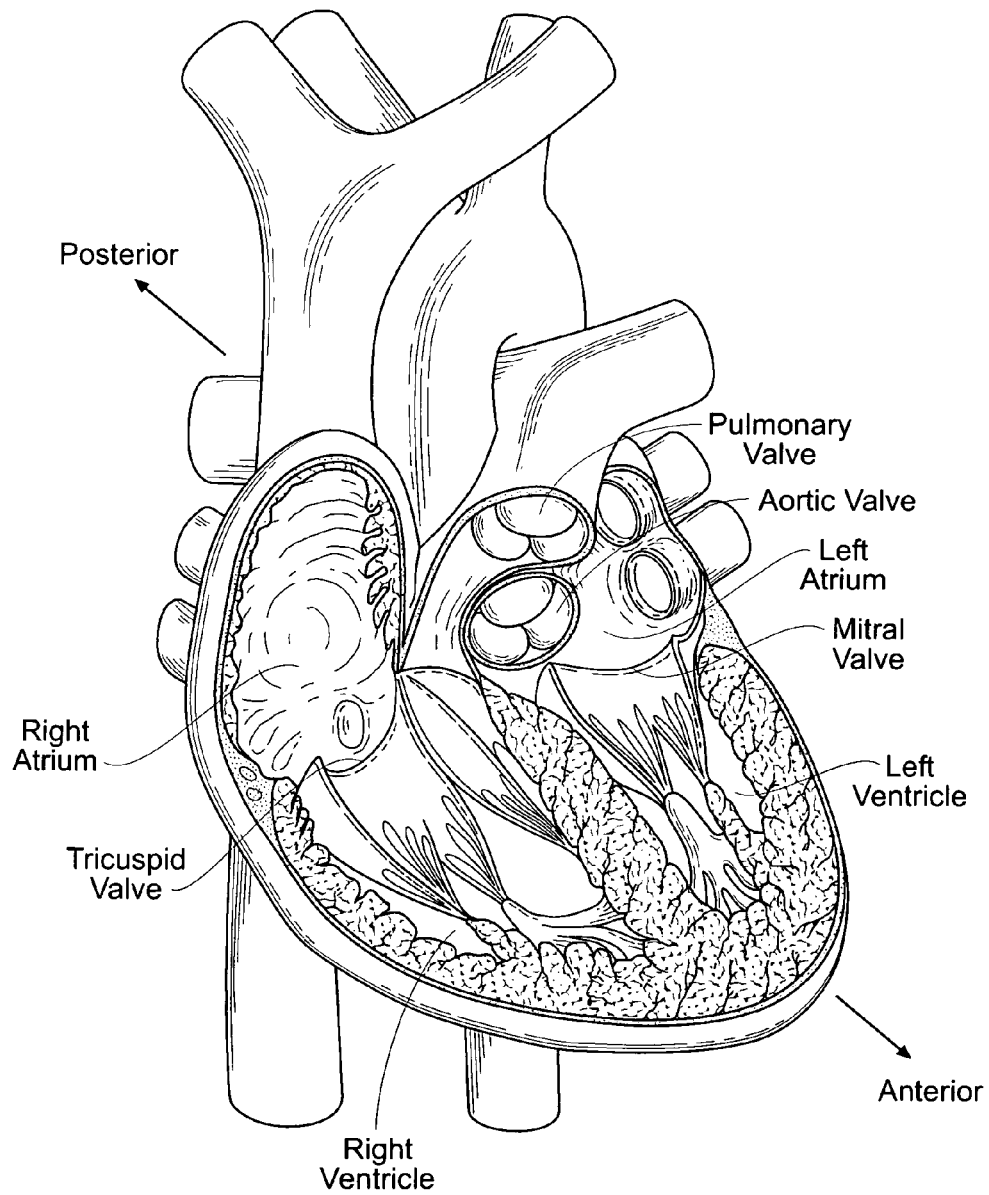
FIG. 1A is a perspective, anterior anatomic view of the interior of a healthy heart.
Figure 1B:
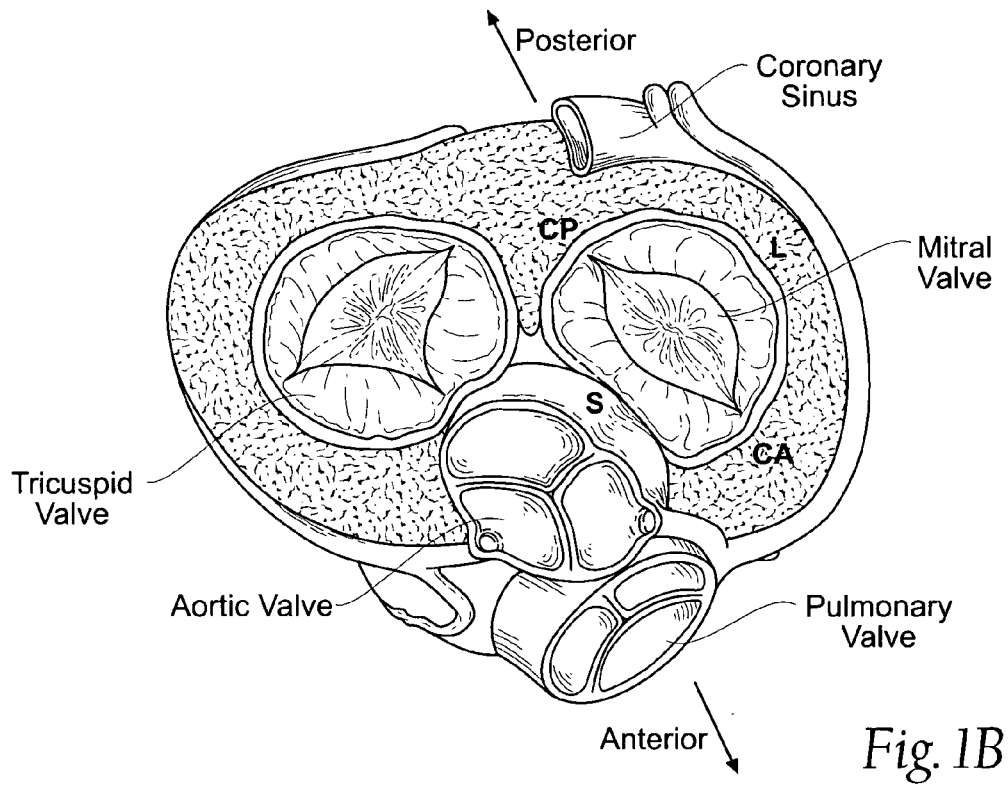
FIG. 1B is a superior anatomic view of the interior of a healthy heart, with the atria removed, showing the condition of the heart valves during ventricular diastole.
Figure 1C:
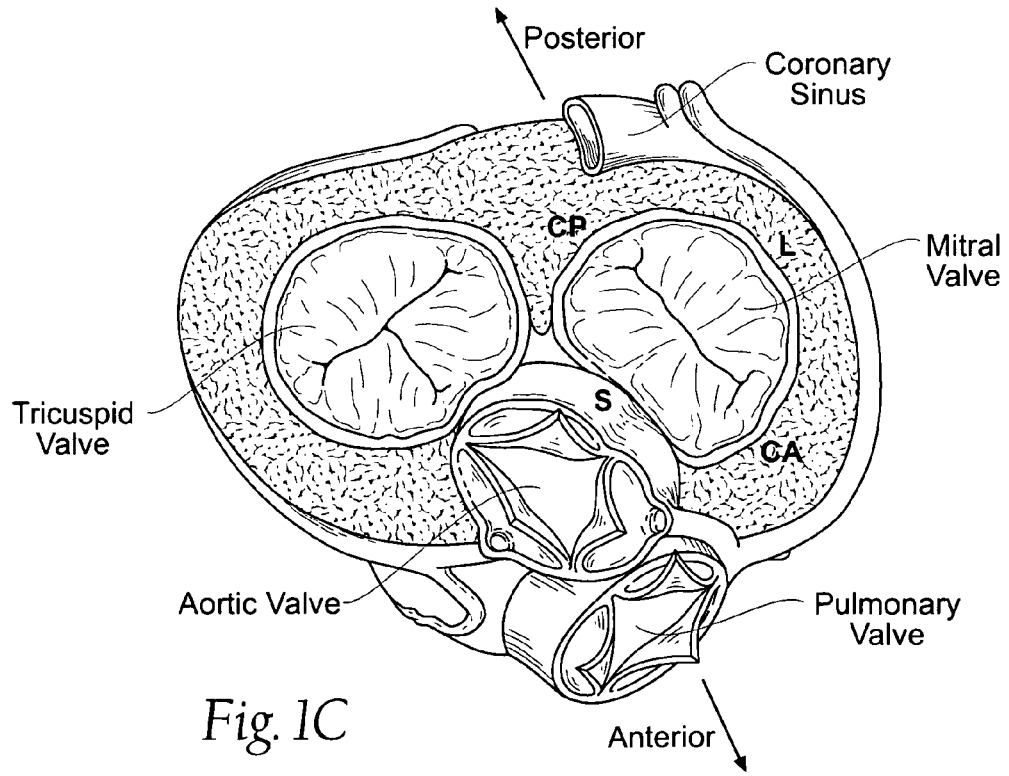
FIG. 1C is a superior anatomic view of the interior of a healthy heart, with the atria removed, showing the condition of the heart valves during ventricular systole.
Figure 1D:
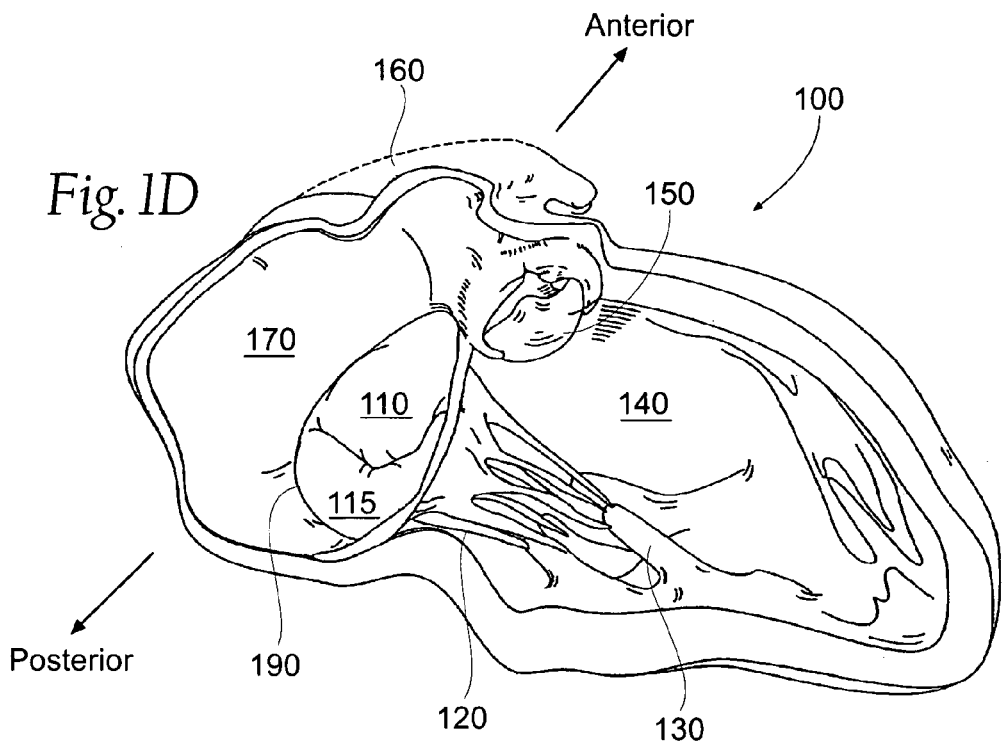
FIG. 1D is a posterior oblique cutaway view of a portion of a human heart, showing a healthy mitral valve during ventricular systole, with the leaflets properly coapting.
Figure 2:
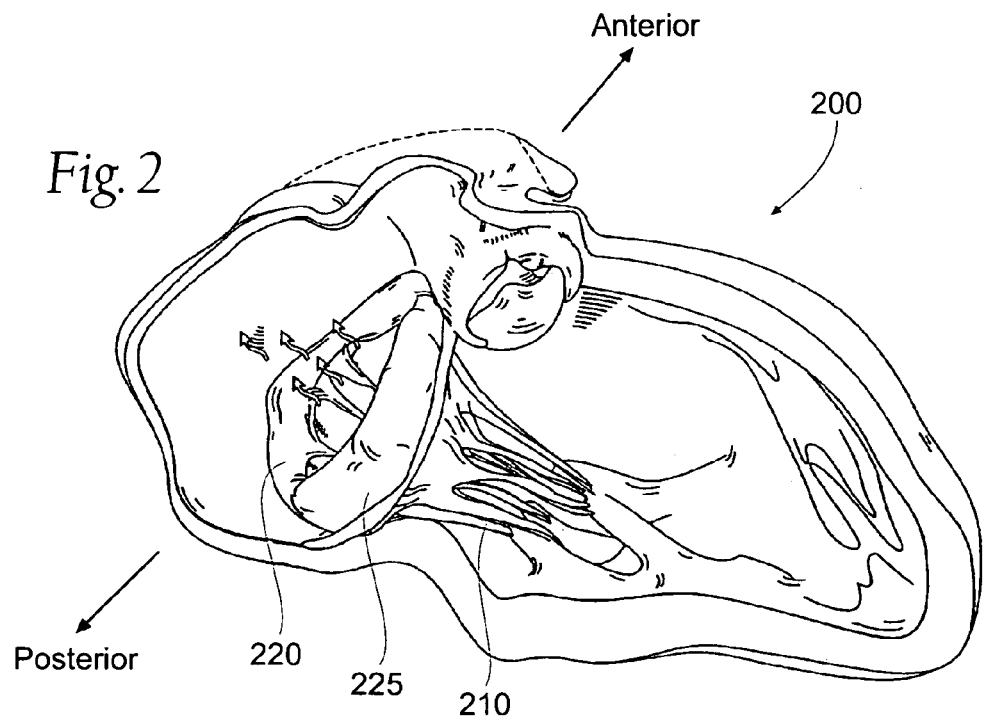
FIG. 2 is a posterior oblique cutaway view of a portion of a human heart, showing a dysfunctional mitral valve during ventricular systole, with the leaflets not properly coapting, causing regurgitation.
Figure 3:
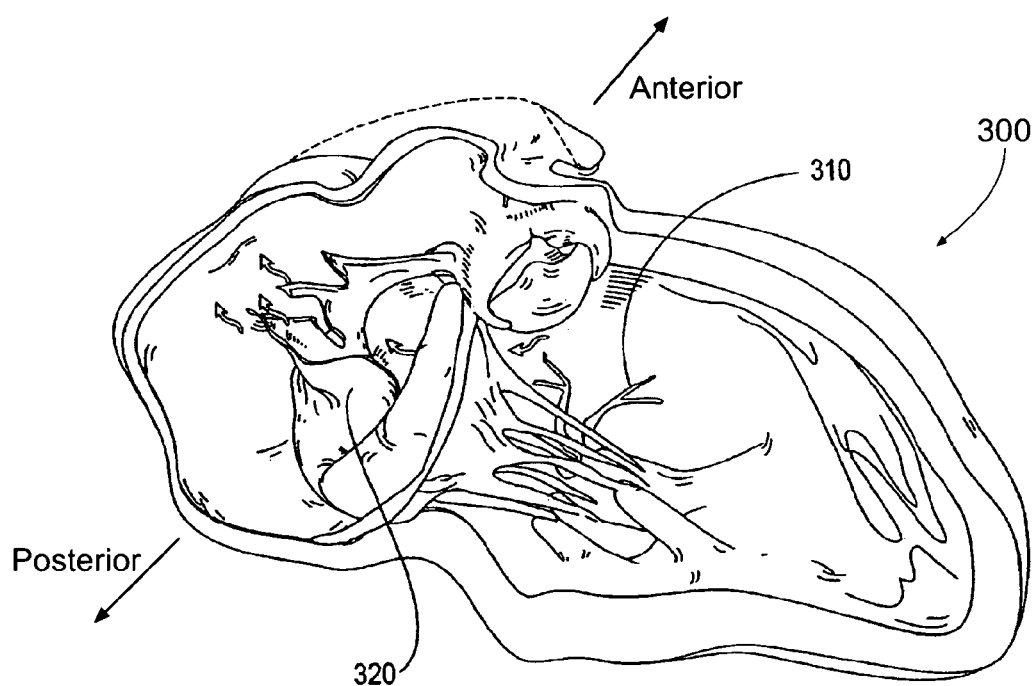
FIG. 3 is a posterior oblique cutaway view of a portion of a human heart, showing a dysfunctional mitral valve during ventricular systole, with the leaflets flailing, causing regurgitation.

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Implants for Retaining a Native Heart Valve Implant

A. Planar Wire-Form Implants

1. Overview

FIGS. 4, 5, and 6 show an implant 400 sized and configured to retain at least one dysfunctional native heart valve leaflet. In use (see, in particular, FIG. 4), the implant 400 rests adjacent all or a portion of the native heart valve annulus, which, in FIG. 4, is in the atrium. The implant 400 includes a scaffold 410, at least a portion of which defines a pseudo-annulus. The scaffold 410 includes a retaining element 420 at or near the pseudo-annulus. The retaining element 420 is sized and shaped to overlay at least a portion of the superior surface at least one native valve leaflet. The implant 400 allows the native leaflets to coexist with the implant 400.

In its most basic form, the components of the implant 400 are made—e.g., by bending, shaping, joining, machining, molding, or extrusion—from a biocompatible metallic or polymer material, or a metallic or polymer material that is suitably coated, impregnated, or otherwise treated with a material or combination of materials to impart biocompatibility. The material is also desirably radio-opaque to facilitate fluoroscopic visualization. The implant material may be rigid, semi-rigid, or flexible.

In the embodiment shown in FIG. 4, the scaffold 410 is sized and configured to rest adjacent all or a portion of the mitral annulus in the atrium. In the illustrated embodiment (FIG. 4), the scaffold 410 forms an annular body that, at least in part, approximates the shape of the native annulus. For this reason, at least a portion of the scaffold 410 is said to define a pseudo-annulus. The scaffold 410 includes the retaining element 420, which extends from the periphery of the scaffold 410 radially into the pseudo-annulus.

The retaining element 420 is sized and configured (see FIG. 4) to overlay the superior surface of at least one native valve leaflet. In the illustrated embodiment, the retaining element 420 overlays regions of both leaflets. However, the retaining element 420 could be sized, configured, and oriented to overlay all or a portion of one leaflet or both leaflets. The size, configuration, and orientation of the retaining element 420 can vary, depending on patient needs, as will be described in greater detail later.

When installed adjacent a mitral valve annulus, during ventricular systole the retaining element 420 exerts a restraining force on the superior surface of the leaflet or leaflets it overlays, resisting deflection of the leaflet or leaflets into the atrium and preventing leaflet eversion and/or prolapse as well as retrograde flow of blood through the valve during ventricular systole from the ventricle into the atrium. The restraining force also serves to keep valve leaflets tightly shut during peak ventricular systolic pressures. The retaining element 420 thus serves as a "backstop" for the leaflet or leaflets it overlays. During ventricular diastole this restraining force goes to zero and the retaining element 420 does not prevent opening of the native valve leaflet or leaflets during antegrade flow. During ventricular diastole, the native valve leaflet or leaflets open normally so that blood flow occurs from the atrium into the ventricle. The implant 400 thereby restores normal one-way function to the valve.

As shown in FIGS. 5 and 6, in the illustrated embodiment, the scaffold 410 and the retaining element 420 are shaped from a continuous length of wire-formed material. The shape and materials of the scaffold 410 and retaining element 420 provide the implant 400 with spring-like characteristics. The retaining element 420 is shaped so that, during ventricular systole, it elastically resists eversion and/or prolapse of the leaflet or leaflets.

2. Fixation of Implants

The spring-like bias of the implant 400 facilitates compliant fixation of the outer periphery of the implant 400 to or near the annulus. The scaffold 410 of the implant 400 dynamically conforms to the shape of the anatomy.

As FIGS. 5 and 6 show, the scaffold 410 can also include supra-annular contact structures 440. The structures 440 are appended to the scaffold 410 to provide multiple contact regions between the implant 400 and the atrial wall, above the valve annulus. The multiple regions of contact that the structures 440 provide uniformly distributes the resting forces of the implant, and help to prevent erosion of the atrial walls and migration of the implant.

Alternatively or in combination with the supra-annular structures 440, the implant 400 can include infra-annular contact struts 430. The struts 430 are appended to the scaffold 410, extending below the plane of the annulus into the ventricular chamber. The struts 430 are preferably configured to extend through the valve orifice on narrow connecting members, so that they will not interfere with the opening and closing of the valve. The struts 430 fix and stabilize the implant within the annulus.

In this arrangement, the struts 430 are desirably sized and configured to contact tissue near or within the mitral valve annulus to brace the retaining structure 420 to resist leaflet eversion and/or prolapse during ventricular systole. In this arrangement, it is also desirable that the scaffold 410 be "elastic," i.e., the material of the scaffold 410 is selected to possess a desired spring constant. This means that the scaffold 410 is sized and configured to possess a normal, unloaded, shape or condition, in which the scaffold 410 is not in net compression, and the struts 450 are spaced apart farther than the longest cross-annulus distance between the tissue that the struts 430 are intended to contact. In the illustrated embodiment (FIG. 4), the scaffold 410 shown resting along the major (i.e., longest) axis of the mitral valve annulus, with the struts 430 contact tissue at or near the leaflet commissures. However, other orientations are possible. The struts 430 need not rest at or near the leaflet commissures, but may be significantly removed from the commissures, so as to gain padding from the leaflets. The spring constant imparts to the scaffold 410 the ability to be elastically compressed out of its normal, unloaded condition, in response to external compression forces applied at the struts 430. The scaffold 410 is sized and configured to assume an elastically loaded, in net compression condition, during which the struts 430 are spaced apart a sufficiently shorter distance to rest in engagement with tissue at or near the leaflet commissures (or wherever tissue contact with the struts 430 is intended to occur) (see FIG. 9A or 9B). When in its elastically loaded, net compressed condition (see FIGS. 9A and 9B), the scaffold 410 can exert forces to the tissues through the struts 430. These forces hold the scaffold 410 (and thus the retaining element 420 itself) against migration within the annulus. Furthermore, when the struts 430 are positioned at or near the commissures, they tend to outwardly displace tissue and separate tissue along the major axis of the annulus, which also typically stretches the leaflet commissures, shortens the minor axis, and/or reshapes surrounding anatomic structures. The scaffold 410 can also thereby reshape the valve annulus toward a shape more conducive to leaflet coaptation. It should be appreciated that, in order to be therapeutic, the implant 400 may only need to reshape the annulus during a portion of the heart cycle, such as during ventricular systolic contraction. For example, the implant may be sized to produce small or negligible outward displacement of tissue during ventricular diastole when the tissue is relaxed, but restrict the inward movement of tissue during ventricular systolic contraction.

As just described, different forms of heart valve treatment can be provided using a single implant 400.

Implants having one or more of the technical features just described, to thereby function in situ as a backstop or retainer for native leaflets, may be sized and configured in various ways. Various illustrative embodiments will now be described.

Figure 7:
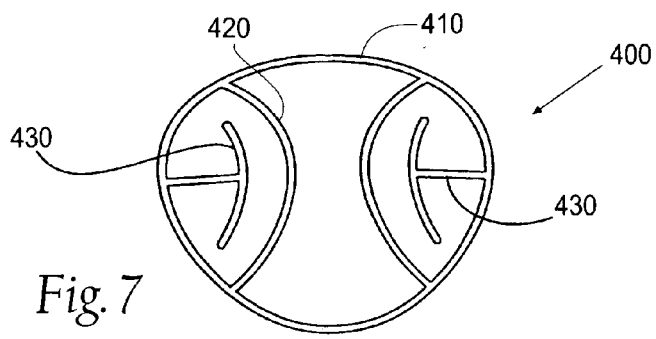
FIG. 7 is a top view of another illustrative wire form implant of the type shown in FIG. 6.

FIG. 7 shows another illustrative embodiment of an implant 400 including a scaffold 410 that defines a pseudo-annulus and a retaining element 420 that functions as a leaflet retainer 420. In FIG. 7, the implant 400 is shown in a flattened condition. The implant 400 includes infra-annular struts 430. Upon deployment, the struts 430 contact tissue near or within the heart valve annulus, and, in particular, between or nearly between the commissures of the leaflets, and extend into the ventricular side of the valve. As before described, the struts 430 function to brace and secure the implant in situ.

Figure 8:
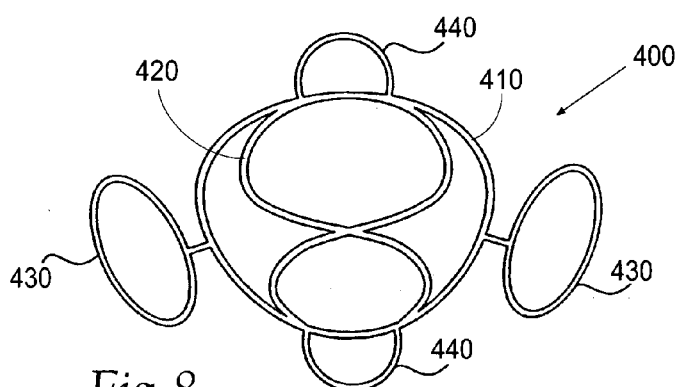
FIGS. 8 and 9 are top views of illustrative wire form implants of the type shown in FIGS. 4 and 5, which include retaining elements to resist eversion and/or prolapse of a native valve leaflet, and which also include both infra-annular struts and tabs and supra-annular pads to fix the position of the implants in a valve annulus.

FIG. 8 shows yet another illustrative embodiment of an implant 400 including a scaffold 410 that defines a pseudo-annulus and a retaining element 420 that functions as a leaflet retainer. The implant 400 also includes infra-annular struts 430. In addition, the implant 400 includes supra-annular contact structures 440, used to disperse the loads experienced by the implant throughout the atrium.

Figure 9:
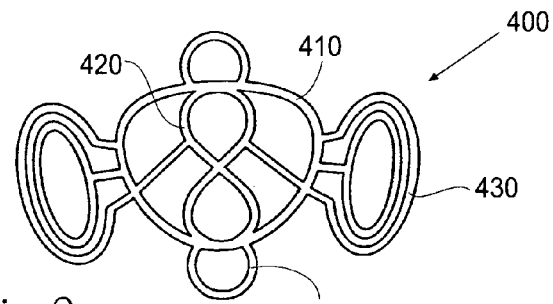

FIG. 9 shows other illustrative embodiment of an implant 400 including a scaffold 410 that defines a pseudo-annulus and a retaining element 420 that functions as a leaflet retainer. In FIGS. 8 and 9, the retaining element 420 extends across the interior of the implant in a figure eight pattern and has two support struts 430. Like the implant shown in FIG. 8, the implant 400 in FIG. 9 includes a plurality of infra-annular struts 430 and a plurality of supra-annular contact structures 440 that brace, fix, and stabilize the implants in situ.

Figure 10:
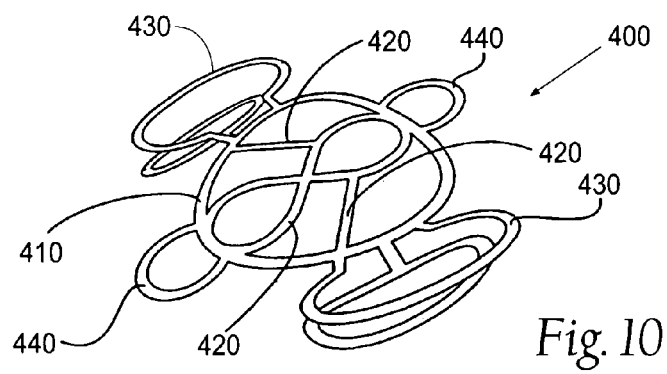
FIG. 10 is a perspective view of the implant shown in FIG. 9.
Figure 11:
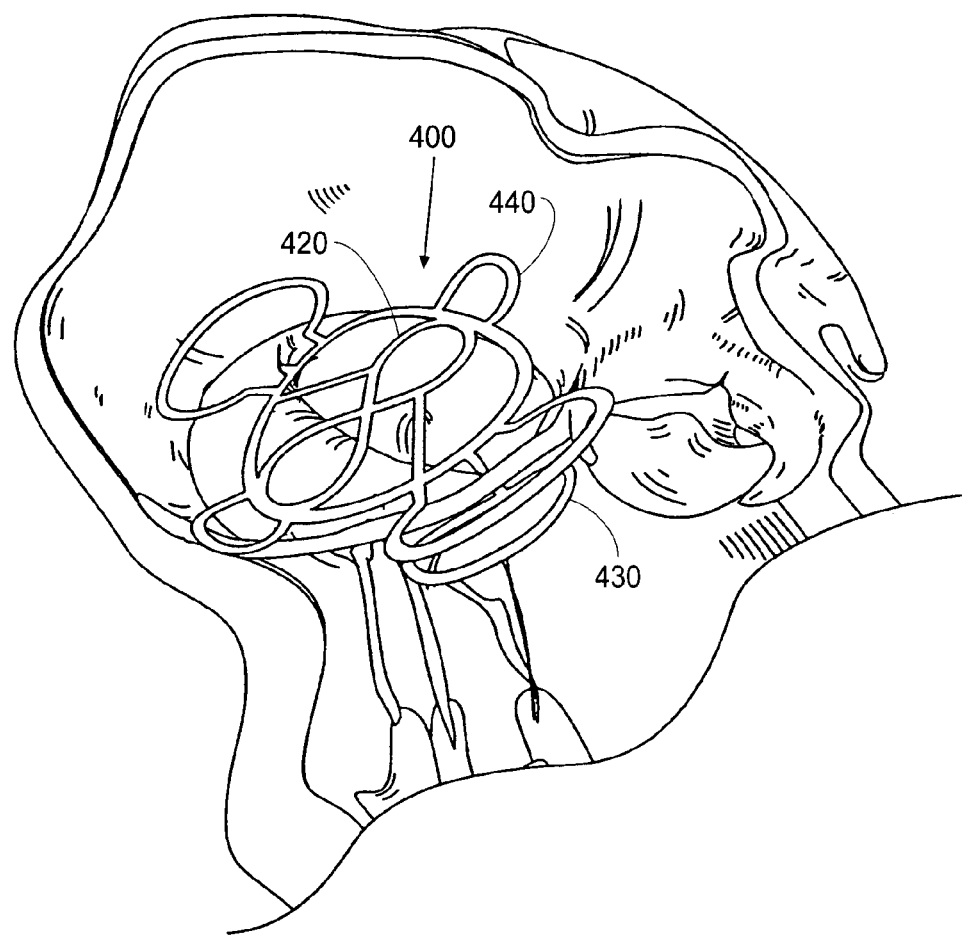
FIG. 11 is a perspective, anatomic view of the wire form implant shown in FIG. 10, the implant being shown installed on a mitral valve annulus.

As can be seen in the perspective view in FIG. 10, one or more of the struts 430 can include a superior component that rests on the atrial side of the valve, and an inferior component that rests on the ventricular side of the valve (see FIG. 11). In this arrangement, the struts 430 place the implant near or within a heart valve annulus, e.g., between the commissures of the leaflets. As before described, the shape and tension of the scaffold 410 can apply a force through the struts 430 that outwardly displaces tissue and stretches the annulus. The displacement of the tissue can remodel the annulus and promote normal valve function, free of eversion and/or prolapse, through a different mechanism than the retaining elements 420.

Any number of supra-annular contact structures 440 can also be used, to disperse the loads experienced by the implant throughout the atrium.

Figure 15:
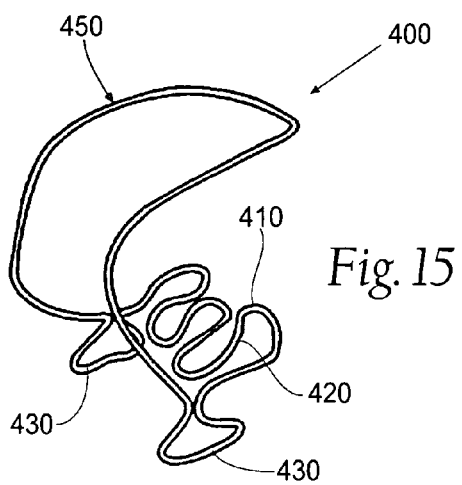
FIG. 15 is a perspective view of an illustrative wire form implant of the type shown in FIGS. 4 and 5, which include retaining elements to resist eversion and/or prolapse of a native valve leaflet, and which also include frameworks to orient and stabilize the position of the implants in a valve annulus.

As FIG. 15 shows, a given implant 400 can include one or more auxiliary structures 450 to orient and stabilize the implant 400 within the left atrium. In FIG. 15, the implant 400 includes, in addition to the scaffold 410 and the retaining element 420, an orientation and stabilization framework 450. The framework 450 rises from the scaffold 410 above the retaining element 420, e.g., with two substantially parallel arched wires, which connect to form a semicircular hoop above the restraining element 420. The framework 450 helps to accurately position the implant 400 within the atrium, and also helps to secure the implant 400 within the atrium.

Preferably the framework 450 does not interfere with atrial function, but instead is compliant enough to contract with the atrium. As such, the implant 400 may have nonuniform flexibility to improve its function within the heart.

Additionally, the implant 400 of FIG. 15 has infra-annular struts 430 that contact tissue near or within the heart valve annulus to brace the implant 400 and assist in positioning and anchoring of the implant.

The implant 400 may be additionally fixed to the annulus in various auxiliary ways. For example, the implant 400 may be secured to the annulus with sutures or other attachment means (i.e. barbs, hooks, staples, etc.). Still, the position and orientation of the implant is desirably braced or fixed by structures appended to or carried by the implant itself, obviating reliance upon such auxiliary fixation measures.

In FIG. 15, the retaining element 420 is sized and configured to cover the superior surface of a single leaflet.

Figure 18:
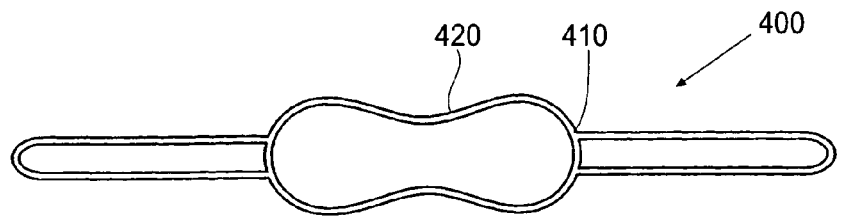
FIGS. 18 and 19 are top views of illustrative embodiments of implants of the types shown in FIGS. 5 and 6, showing implants that are narrow and do not peripherally rest on the entire valve annulus.
Figure 19:
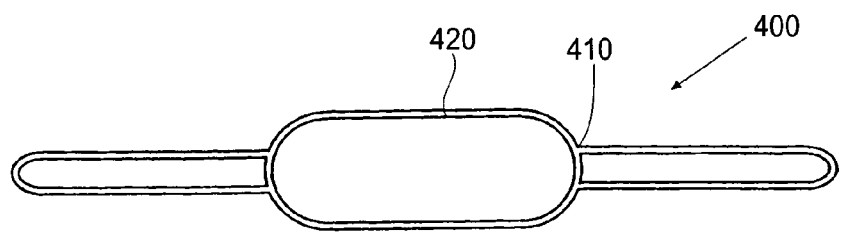

FIGS. 18 and 19 show other illustrative embodiments of implants 400 sized and configured to function as leaflet retainers. In these embodiment, each implant 400 includes a narrow leaflet retaining element 420. The narrow leaflet retaining elements 420 span the annulus, but the associated scaffold 410 need not peripherally follow the entire annulus.

3. Deployment of Wire Form Implants

The implant 400 may be delivered percutaneously, thoracoscopically through the chest, or using open heart surgical techniques. If delivered percutaneously, the implant 400 may be made from a superelastic material (for example superelastic Nitinol alloy) enabling it to be folded and collapsed such that it can be delivered in a catheter, and will subsequently self-expand into the desired shape and tension when released from the catheter. The deployment of an implant in this fashion will now be described.

Figure 12:
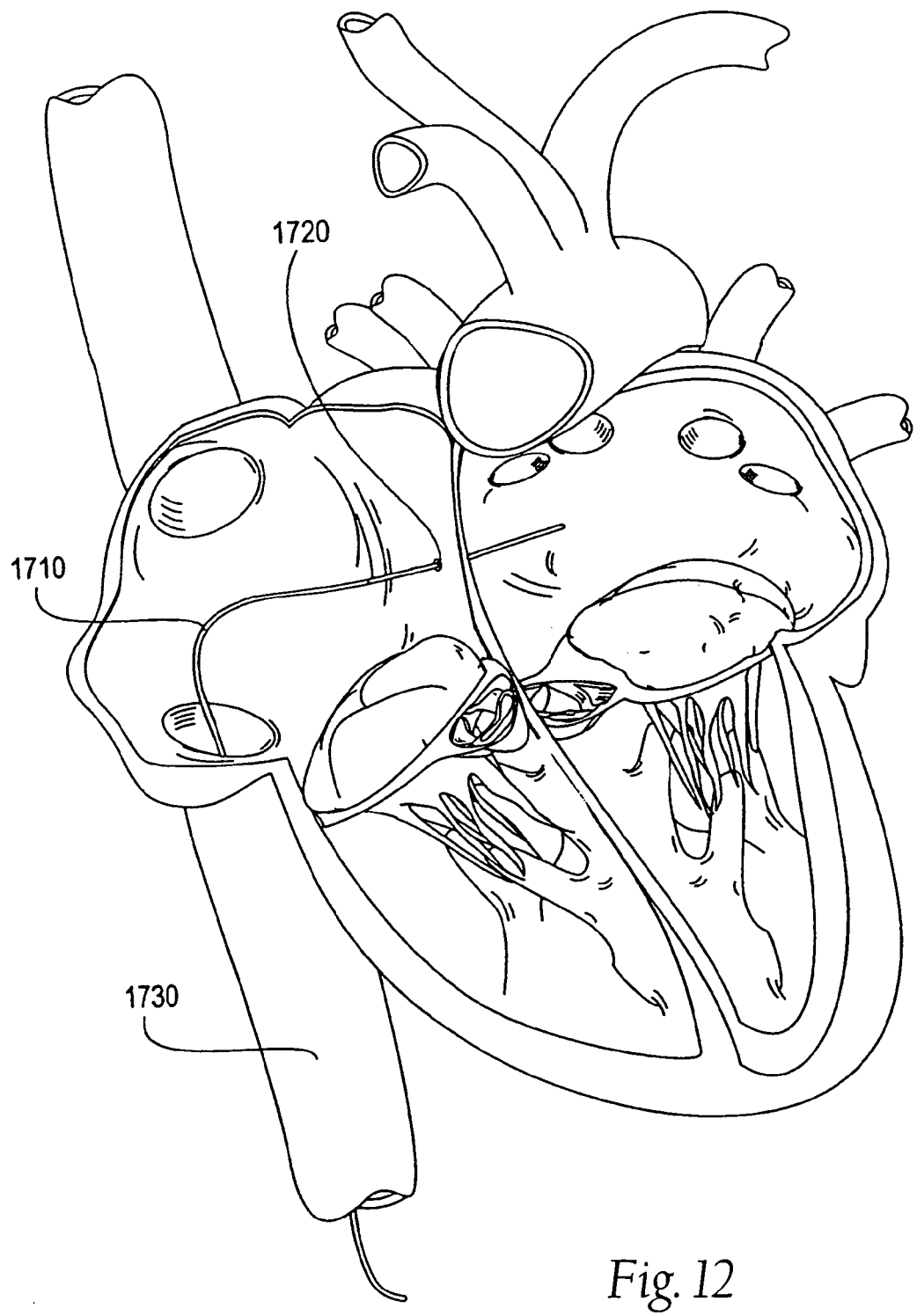
FIGS. 12 to 14 are perspective, anatomic views showing the intravascular introduction and deployment of the implant shown in FIG. 11 on a mitral valve annulus.
Figure 13:
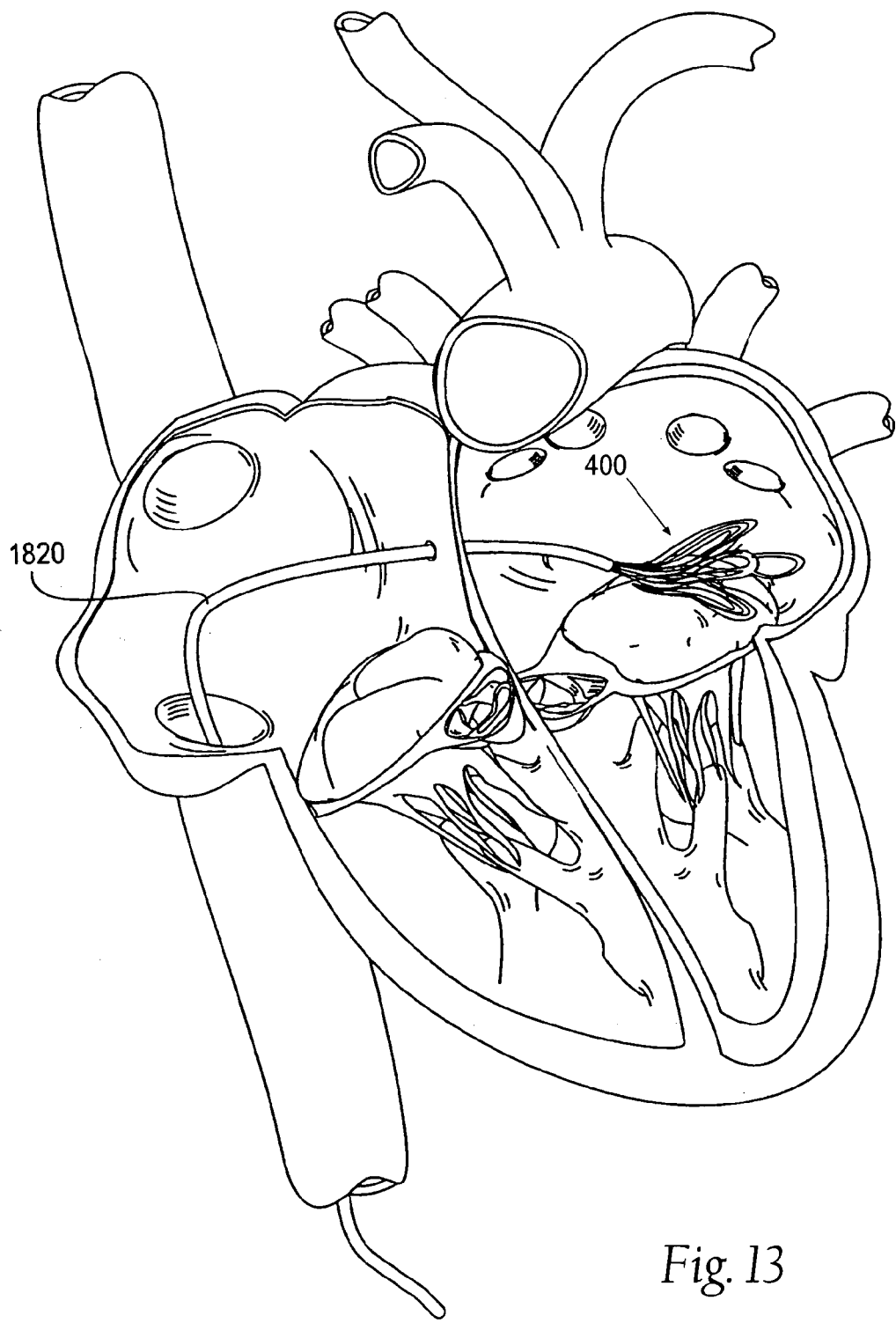
Figure 14:
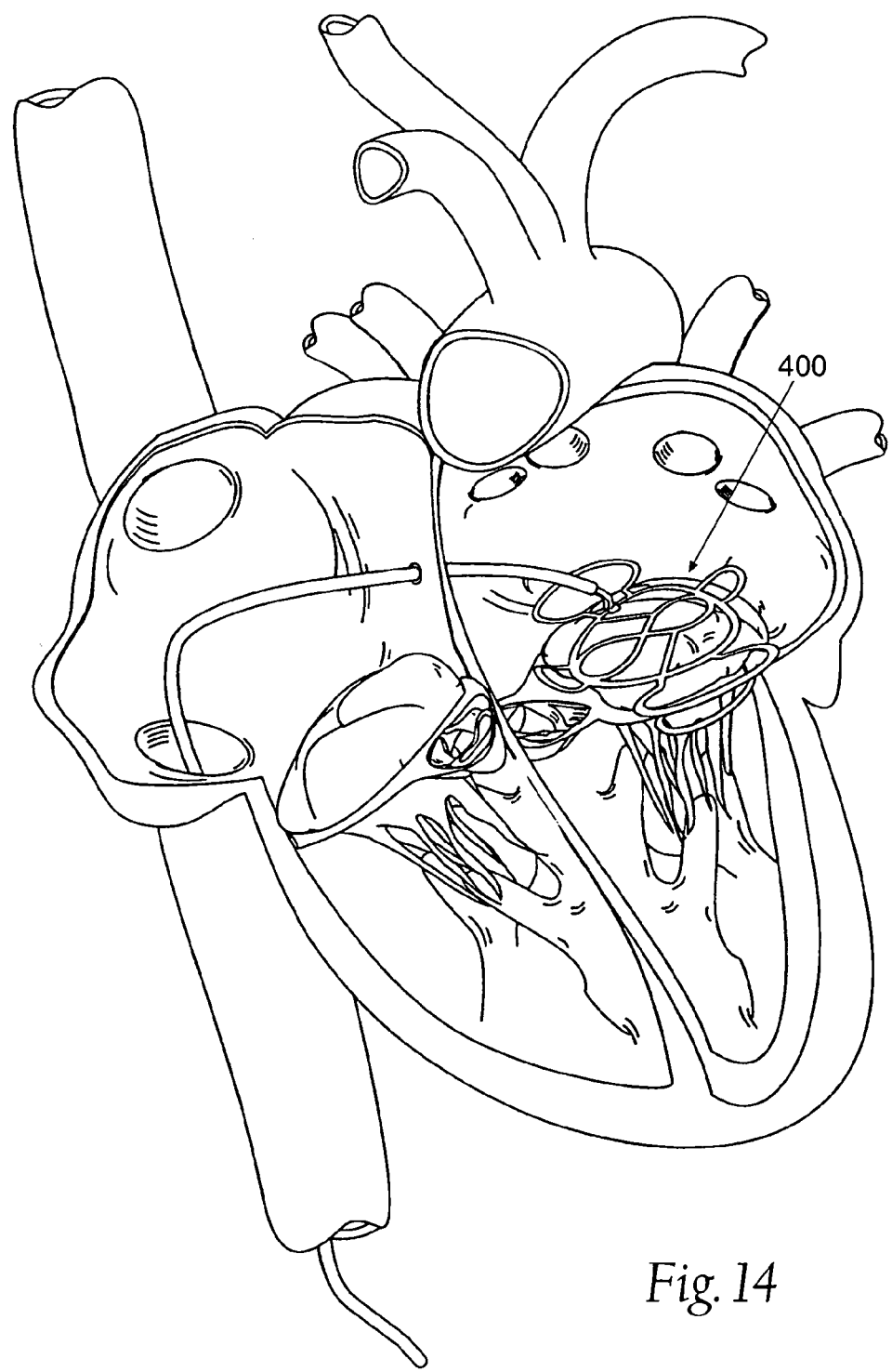

FIGS. 12 to 14 show a sequence of steps for a catheter-based, percutaneous deployment of an implant 400 having the technical features described. Percutaneous vascular access is achieved by conventional methods into the femoral or jugular vein. Under image guidance (e.g., fluoroscopic, ultrasonic, magnetic resonance, computed tomography, or combinations thereof), a first catheter (not shown) is steered through the vasculature into the right atrium. A needle cannula carried on the distal end of the first catheter is deployed to pierce the septum between the right and left atrium. A guide wire 1710 is advanced trans-septally through the needle catheter into the left atrium. The first catheter is withdrawn, leaving the guide wire 1710 behind. FIG. 12 shows the guide wire 1710 introduced through the vena cava 1730 and into the right atrium, and then through the septum 1720 between the right and left atriums, into the left atrium.

As FIG. 13 shows, under image guidance, an implant delivery catheter 1820 is advanced over the guide wire 1710 into the left atrium into proximity with the mitral valve. Alternatively, the implant delivery catheter 58 can be deployed trans-septally by means of surgical access through the right atrium.

The implant delivery catheter 1820 carries within it a wire-form implant 400 of a type shown in FIGS. 10 and 11, previously described. The implant 10 is constrained within the catheter 1820 in a collapsed, straightened condition. A push rod within the catheter 1820 expels the implant (see FIG. 13). Free of the catheter 1820, the implant 400 will expand, as FIG. 14 shows. Progressively freed from the catheter 1820, the implant 400 shapes and seats about the annulus, as the struts 430 seat within the commissures and the retaining elements 420 extend over the leaflets. The implant can also be positioned or repositioned under image guidance within the left atrium using a catheter-deployed grasping instrument.

B. Wire-Form Mesh Implants

Figure 17:
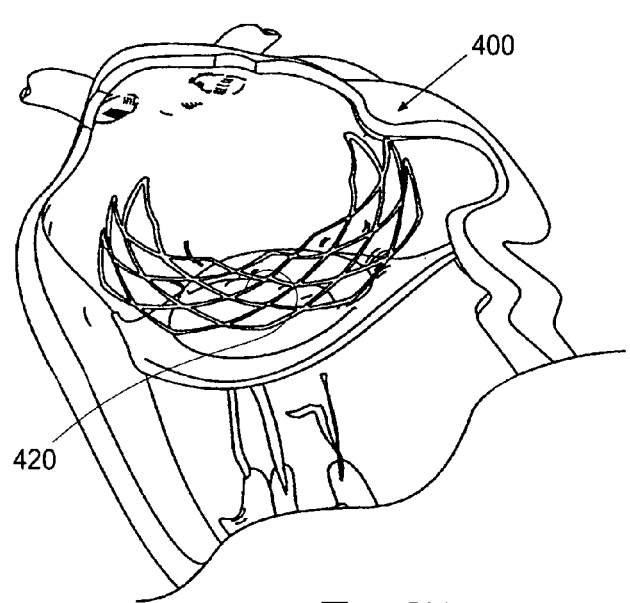
FIG. 17 is a perspective, anatomic view of the wire-form mesh implant shown in FIG. 16 installed on a mitral valve annulus.
Figure 16:
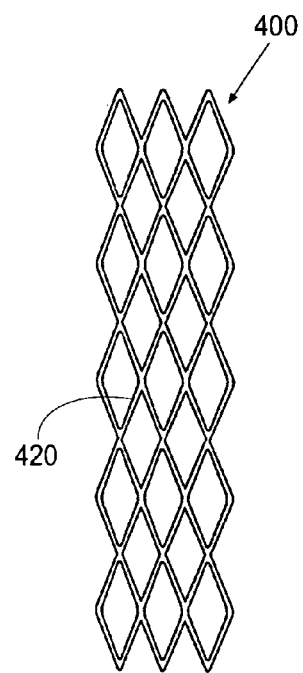
FIG. 16 is a top view of wire-form mesh implant that resists eversion and/or prolapse of a native valve leaflet.

FIGS. 16 and 17 show another embodiment of an implant 400 including a scaffold 410 that defines a pseudo-annulus and a retaining element 420 that functions as a leaflet retainer. In this embodiment, the retaining element 420 includes wire-form mesh that has been shaped to fit the heart anatomy (see FIG. 16). The wire-form mesh can be secured within the atrium with sutures or other attachment means (i.e. barbs, hooks, staples, etc.). Alternatively, the body of the wire-form mesh can be secured by spring action between the body of the implant and the walls of the heart.

Figure 20:
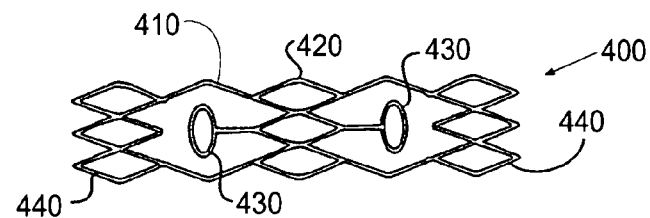
FIG. 20 is a top view of an illustrative embodiment of a wire-form mesh implant of the type shown in FIGS. 16 and 17, being shown in a flattened condition for intravascular deployment, which, upon deployment, resists eversion and/or prolapse of a native valve leaflet, and which also include an auxiliary structure to orient and stabilize the position of the implants in a valve annulus, the implant in FIG. 20 also including infra-annular struts and tabs to fix the position of the implant in the valve annulus.
Figure 21:
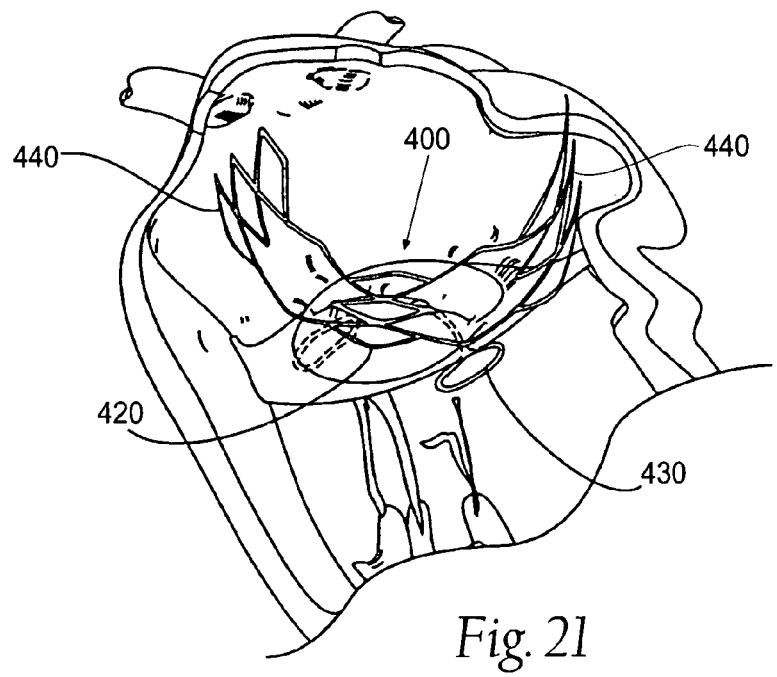
FIG. 21 is a perspective, anatomic view of the wire-form mesh implant shown in FIG. 20, installed on a mitral valve annulus.

In FIG. 20, another illustrative embodiment of an implant 400 including a scaffold 410 that defines a pseudo-annulus and a retaining element 420. The implant 400 is shown in a flattened out condition. FIG. 21 shows the implant 400 shown in FIG. 20 after deployment in a left atrium. The implant 400 includes a leaflet retaining element 420, upwardly extending stabilization arch structures 440, as well as infra-annular struts 430, shaped and configured as previously described. The arch structures 440 and struts 430 cooperate to orient and stabilize the implant in the desired position for retaining the valve leaflets.

Figure 22:
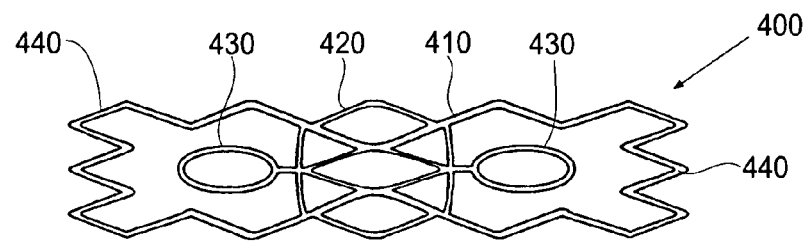
FIGS. 22, 23, and 24 are top views of illustrative embodiments of wire-form mesh implants of the type shown in FIG. 20, which resist eversion and/or prolapse of a native valve leaflet, and which also include a combination of auxiliary structures and infra-annular struts and tabs to fix, orient, and stabilize the position of the implants in a valve annulus, the implants being shown in a flattened condition for intravascular deployment.
Figure 23:
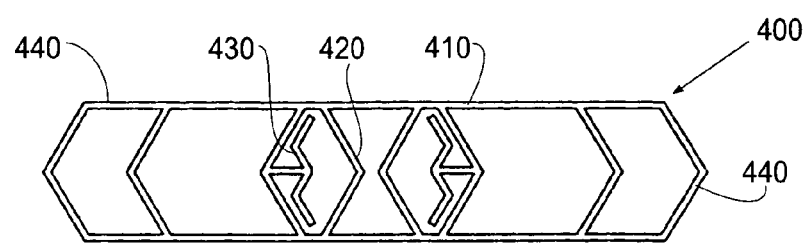
Figure 24:
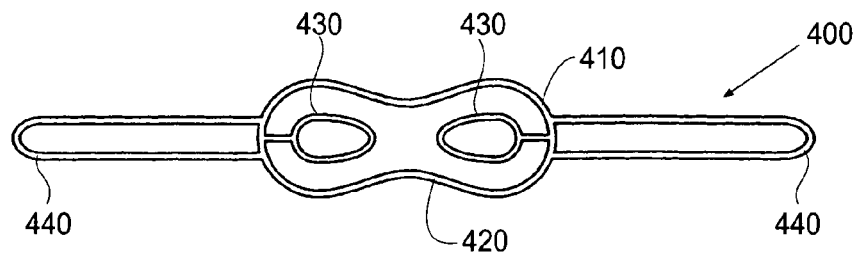
Figure 25:
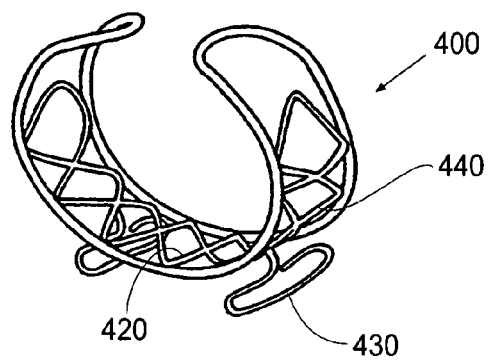
FIG. 25 is a perspective view of illustrative embodiments of wire-form mesh implants of the type shown in FIG. 20, which resist eversion and/or prolapse of a native valve leaflet, and which also include a combination of auxiliary structures and infra-annular struts and tabs to fix, orient, and stabilize the position of the implants in a valve annulus, the implants being shown in an expanded condition after intravascular deployment.

FIGS. 22, 23, and 24 show illustrative embodiments of other implants 400 of the type shown in FIGS. 20 and 21 in flattened out conditions. Each of these implants 400 include a scaffold 410 that defines a pseudo-annulus and a retaining element 420. In these embodiments, the implants 400 include, in addition to a leaflet retaining element 420, a plurality of arch structures 440 that, when deployed, contact the interior of the atrium to support and align the implant 400, as well as infra-annular struts 430 that contact tissue near or within the heart valve annulus to brace the retaining structure 420 to resist leaflet eversion and/or prolapse during ventricular systole. FIG. 25 shows various illustrative embodiments of an implant 400 in a deployed conditioned.

While the new devices and methods have been more specifically described in the context of the treatment of a mitral heart valve, it should be understood that other heart valve types can be treated in the same or equivalent fashion. By way of example, and not by limitation, the present systems and methods could be used to resist or prevent retrograde flow in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. An implant that retains a native heart valve leaflet within a heart chamber to resist retrograde flow comprising:
    a scaffold sized and configured to rest adjacent all or a portion of a native heart valve annulus, at least a portion of the scaffold defining a pseudo-annulus and including a retaining structure near or within the pseudo-annulus that is sized and shaped to overlay at least a portion of one or more native valve leaflets,
    the scaffold further including spaced-apart struts sized and configured to contact tissue near or within the heart valve annulus to brace the retaining structure to resist leaflet eversion and/or prolapsed, and
    an auxiliary structure to orient and stabilize the scaffold with the heart chamber, the auxiliary structure comprising a framework that rises above the scaffold including two substantially parallel arched wires that connect to form a semicircular hoop above the scaffold to position the scaffold within the heart chamber, the framework being compliant to contract with the heart chamber.

2. An implant according to claim 1
    wherein the retaining structure comprises a wire-form structure.

3. An implant according to claim 1
    wherein at least one of the struts comprises a wire-form structure.

4. An implant according to claim 1
    wherein the retaining structure and the struts each comprises a wire-form structure.

5. An implant according to claim 1
    wherein the scaffold is collapsible for placement within a catheter.

6. An implant according to claim 1
    wherein at least one of the struts carries a structure sized and configured to increase a surface area of contact with tissue at, above, or below the annulus.

7. An implant according to claim 1 wherein the scaffold includes a material and a shape to provide a spring-like bias to enable compliant contact with tissue near or within the heart valve annulus.

8. An implant according to claim 1 wherein the struts reshape the heart valve annulus.

9. An implant according to claim 1 wherein the struts apply tension to tissue to reshape the heart valve annulus.

10. An implant according to claim 1 wherein the struts displace tissue to reshape the heart valve annulus.

11. An implant according to claim 1 further including a second heart valve treatment element appended to the scaffold to affect a heart valve function.

12. An implant according to claim 11 wherein the second heart valve treatment element includes means for reshaping the heart valve annulus for leaflet coaptation.

13. An implant according to claim 11 wherein the second heart valve treatment element includes means for separating tissue along an axis of the heart valve annulus for leafleted coaptation.

\* \* \* \* \*